(12) United States Patent
Ross et al.

(10) Patent No.: US 7,201,756 B2
(45) Date of Patent: Apr. 10, 2007

(54) DEVICE AND METHOD TO ASSIST IN ARTHROSCOPIC REPAIR OF DETACHED CONNECTIVE TISSUE

(76) Inventors: Herbert Earl Ross, 15375 Classic Dr., Bath, MI (US) 48808; Mitchell Theodore Copeland, 1133 Sundial Rd., Grand Junction, CO (US) 81505

( * ) Notice: Subject to any disclaimer, the term of this patent is extended or adjusted under 35 U.S.C. 154(b) by 0 days.

(21) Appl. No.: 10/395,655

(22) Filed: Mar. 24, 2003

(65) Prior Publication Data

US 2004/0193172 A1 Sep. 30, 2004

(51) Int. Cl.
*A61B 17/58* (2006.01)
*A61B 17/60* (2006.01)

(52) U.S. Cl. .......................................... 606/96; 606/98
(58) Field of Classification Search .................. 606/96, 606/88, 103, 80, 87, 86, 81, 98, 179, 102, 606/148, 105
See application file for complete search history.

(56) References Cited

U.S. PATENT DOCUMENTS

| | | | |
|---|---|---|---|
| 5,112,337 A | 5/1992 | Paulos et al. | |
| 5,163,940 A * | 11/1992 | Bourque | ..................... 606/96 |
| 5,269,786 A | 12/1993 | Morgan | |
| 5,330,468 A * | 7/1994 | Burkhart | ..................... 606/96 |
| 5,350,383 A * | 9/1994 | Schmieding et al. | ......... 606/96 |
| 5,562,664 A * | 10/1996 | Durlacher et al. | ............ 606/96 |
| 5,575,801 A | 11/1996 | Habermeyer et al. | |
| 5,584,839 A | 12/1996 | Gieringer | |
| 5,601,562 A * | 2/1997 | Wolf et al. | .................... 606/86 |
| 5,624,446 A | 4/1997 | Harryman, II | |
| 5,700,266 A | 12/1997 | Harryman, II | |
| 5,951,559 A | 9/1999 | Burkhart | |
| 5,993,451 A | 11/1999 | Burkhart | |
| 6,120,511 A * | 9/2000 | Chan | ........................... 606/96 |
| 6,254,606 B1 * | 7/2001 | Carney et al. | ............. 606/102 |
| 6,537,319 B2 * | 3/2003 | Whelan | ................... 623/13.12 |

* cited by examiner

*Primary Examiner*—Pedro Philogene
(74) *Attorney, Agent, or Firm*—John M. Naber; Dickinson Wright PLLC

(57) ABSTRACT

A surgical assist device and method that can be used to assist a surgeon in site selection and suture placement to re-attach the glenoid labrum to the shoulder's glenoid bone. The device and method includes an arcuate shaped bow arm, an angle guide attached to the bow arm at a selected location along the bow arm, a sleeve guide, and a target tool releasably connected to the angle guide. A tip end of the sleeve guide is extended in surgery and is configured to intersect and pass through an aperture of the target tool. The tip end of the sleeve guide includes at least one tooth that embeds in the glenoid bone and holds the sleeve guide in position. A guide pin such as a suture carrier is extended through the sleeve guide. The sleeve guide is then removed leaving the sutures in the correct repair location.

18 Claims, 6 Drawing Sheets

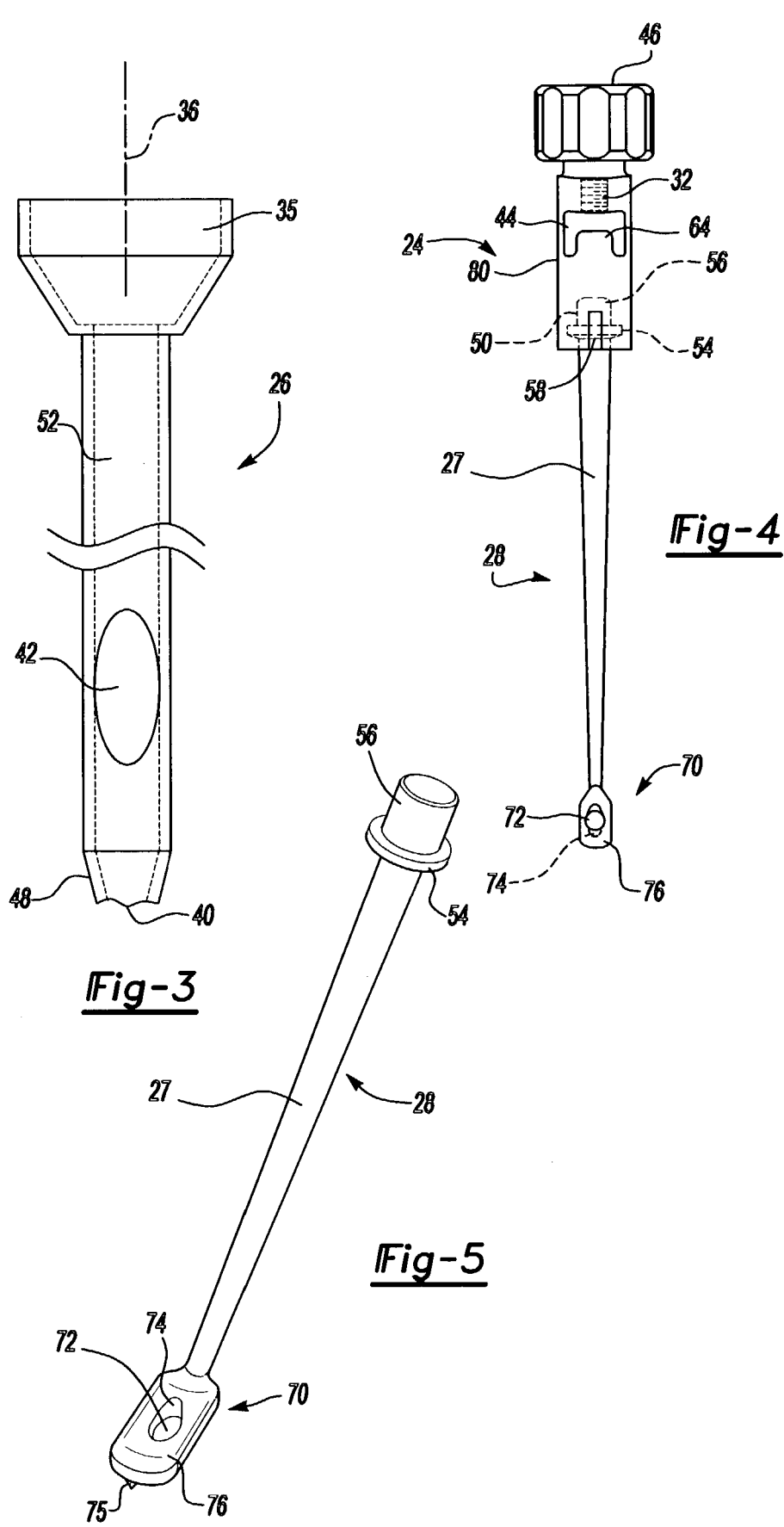

DEVICE AND METHOD TO ASSIST IN ARTHROSCOPIC REPAIR OF DETACHED CONNECTIVE TISSUE

FIELD OF THE INVENTION

The present invention relates generally to the field of orthopedic devices and methods used for repairing detached connective tissue between a ball and socket of a joint, and more specifically a sighting device that can be used to assist a surgeon in locating re-attachment points of the glenoid labrum to the glenoid cavity, along the superior/posterior margin of a glenoid cavity of a shoulder joint.

BACKGROUND OF THE INVENTION

A human shoulder articulates about a loose fitting ball-and-socket joint that allows extremely free movement of the arm relative to the body's trunk. The ball is formed on the head of the humerus, and the socket is formed by a shallow laterally opening glenoid cavity of the scapula bone. The depth of the socket is increased by a circumferential ring of fibrocartilage, the glenoid labrum, to which the head of the humerus is attached by an encircling mass of connective tissue called the articular capsule. Such capsule includes, for example, ligaments and tendons.

There is little area of contact between the ball of the humerus and the glenoid cavity. Nevertheless, there is always a considerable part of the ball of the humerus in contact with the articular capsule. The loose fitting ball-and-socket connection allows the articulating surfaces of the bones to be substantially separated. Since this joint is so loosely constructed, it is frequently dislocated in contact sports. Furthermore, recent studies reveal that athletes who engage in throwing or racquet sports can chronically develop shoulder instability by creating a gradual separation between the cartilage labrum and bony glenoid.

A shoulder can become unstable in any one direction, or it can become unstable in all directions i.e., a global instability. There is greater superior (upper) and posterior (rearward) support for the shoulder joint. Therefore, frequent dislocations occur in an anterior (forward) and inferior (downward) direction. In fact, these dislocations account for ninety percent of shoulder instabilities. An instability can be created by an avulsion (or tearing away) of the glenoid labrum from the superior margins of the glenoid cavity of the glenohumeral joint. From an anterior to posterior direction this capsulolabral separation is known as a SLAP (superior labrum, anterior to posterior) lesion. In other words, a SLAP lesion is an avulsion of the cartilage rim from the superior region of the socket extending posteriorly and anteriorly. A Bankart lesion, which is an avulsion of the glenoid labrum from the anterior and inferior margins of the glenoid cavity, and a rotator cuff lesion, which is an avulsion of the tendon from the humeral head are also common injuries associated with the shoulder joint, and can be a secondary result of superior shoulder instability.

As a result of the anterior shoulder injuries described above, surgical repair of the glenoid labrum is usually required to regain shoulder stability. The standard of care known in the art for many years has been by open shoulder surgery methods and typically involved spreading the muscles overlying the anterior side of the joint and severing some of the connective tissue to provide access to the anterior glenoid rim. In one technique, intersecting holes are drilled in the anterior and lateral faces of the glenoid cavity adjacent to the rim for attaching sutures that secure the detached labrum firmly to the glenoid rim at two or three locations. Over time the labrum re-attaches. Unfortunately, as with most open surgery techniques, morbidity of the repair site can and does frequently occur, resulting in a prolonged healing process.

Arthroscopic surgery can be used to repair a number of gleno-humeral injuries. Repair of the superior glenoid labrum becomes one of the most challenging surgical procedures in all of shoulder surgery. The superior aspect of the glenoid is bounded superiorly by the rotator cuff, which must not be violated. Anteriorly, the biceps tendon conflicts with an anterior superior approach to the superior labrum, and secondary inflammatory reaction caused by an unstable labrum can interfere with the view through the arthroscope.

Abrading the glenoid rim during arthroscopic surgery is essential to create a "healing bed" for the labrum. Nevertheless, different and more invasive techniques for securing the labrum to the glenoid rim area are available. In one technique, one or more staples are used to connect the glenoid labrum to the anterior side of the scapular neck medially of the glenoid cavity. In another technique, the labrum is impaled with a rivet that is driven into the scapular neck. In another technique, blind bores are drilled adjacent to the anterior glenoid rim for specially designed suture anchors. In yet another technique, a hole is drilled through the scapular neck for pin or screw placement to which suture material can be attached, and which is then used to tie the glenoid labrum to the scapular neck.

Although arthroscopic techniques are a great improvement over open shoulder surgery, there remains room for improvement. For example, a problem in arthroscopic glenoid labrum re-attachment is positioning the drilling and securing devices in a fast and efficient manner with minimal trauma to the surrounding tissue. Significant tissue damage can occur from repeated unsuccessful attempts to blindly locate a proper or desired re-attachment site. This surgical site could be as much as four to eight inches (10.16 cm to 20.32 cm) deep from the skin surface depending upon the size and muscular development of the patient. Prior art instruments used to aid locating connective tissue re-attachment sites are known in the art, but are designed for the particular environment found in the knee for anterior and posterior cruciate ligament reconstruction. See generally, U.S. Pat. Nos. 5,269,786; 5,112,337; and 4,920,958. Habermeyer (U.S. Pat. No. 5,575,801) shows an apparatus for arthroscopic rotator cuff repair, but the Habermeyer device does not include a method or device suited for accurate site selection for the re-attachment of the glenoid labrum to the glenoid cavity.

Thus, there is a desire and a need for a device and method to improve site selection and suture placement as required in the repair of lesions of the glenoid labrum to the glenoid cavity in a shoulder, specifically a SLAP lesion repair.

SUMMARY OF THE INVENTION

Accordingly, the device and method in accordance with the present invention improves accuracy, efficiency and therefore a reduction in operative time and tissue damage. This is accomplished by the elimination of "trial and error" placement of the implant formerly associated with surgical arthroscopic repair of a capsulo-labral separation, such as a SLAP (superior labrum, anterior to posterior) lesion, where a portion of the glenoid labrum has been avulsed from the glenoid cavity.

The present invention provides a method and device for accurate site selection and suture placement to re-attach the glenoid labrum to the shoulder's glenoid cavity.

In one embodiment of the present invention, a surgical assist device for use in arthroscopic shoulder surgery includes an arcuate shaped bow arm, an angle guide attached to the bow arm at a predetermined location along the arc of the bow arm, a sleeve guide having a base end slidably attached to the bow arm and a tip end having at least one tooth. A target tool is releasably connected to the angle guide at a first end and includes a second end extending away from the bow arc and having an aperture. The tip end of the sleeve guide is configured to extend to intersect and pass through the aperture of the target tool irrespective of the position of the angle guide on the bow arm. The tooth on the tip of the sleeve guide is embedded in the glenoid bone to be repaired, positioning the sleeve guide in the desired location for surgery.

In another embodiment of the present invention, a method for locating the target location for a glenoid labrum lesion repair in arthroscopic shoulder surgery using a surgical assist device is provided. The surgical assist device comprises an arcuate shaped bow arm, an angle guide attached to the bow arm at a pre-selected location, and a sleeve guide attached to the bow arm. A target tool is attached to the angle guide at a first end and includes an aperture on a second end. The sleeve guide extends outward from the bow arm and has at least one tooth on the outward end and a longitudinally extending bore through its center. The method comprises the steps of inserting the second end of the target tool into the glenoid cavity of a shoulder requiring lesion repair; positioning the aperture of the target tool at a desired location; advancing the sleeve guide towards the glenoid labrum and through the aperture of the target tool until the at least one tooth on the sleeve guide contacts the glenoid bone and is embedded in the glenoid bone, firmly holding the sleeve guide in position.

Other advantages of the present invention will become more apparent to persons having ordinary skill in the art to which the present invention pertains from the following description taken in conjunction with the accompanying figures.

BRIEF DESCRIPTION OF THE FIGURES

The advantages and features will become apparent with reference to the description and drawings below, in which like numerals represent like elements, and in which:

FIG. 3 illustrates an enlarged view of the tip end of the sleeve guide of the present invention;

FIG. 4 illustrates an embodiment the target tool of the present invention;

FIG. 5 illustrates an embodiment of a target tool of the present invention having an angled sight locator;

DETAILED DESCRIPTION OF THE INVENTION

Many of the advantages and features of this invention will become more readily appreciated by reference to the following detailed description, when taken in conjunction with the accompanying drawings. The device of the present invention aids in the placement of a surgical sleeve guide and is generally indicated as a surgical assist device at 20 in FIGS. 1 and 2. Surgical assist device 20 generally includes a sleeve guide 26, an angle guide 24, and an arcuate bow arm 22.

Figure 1:
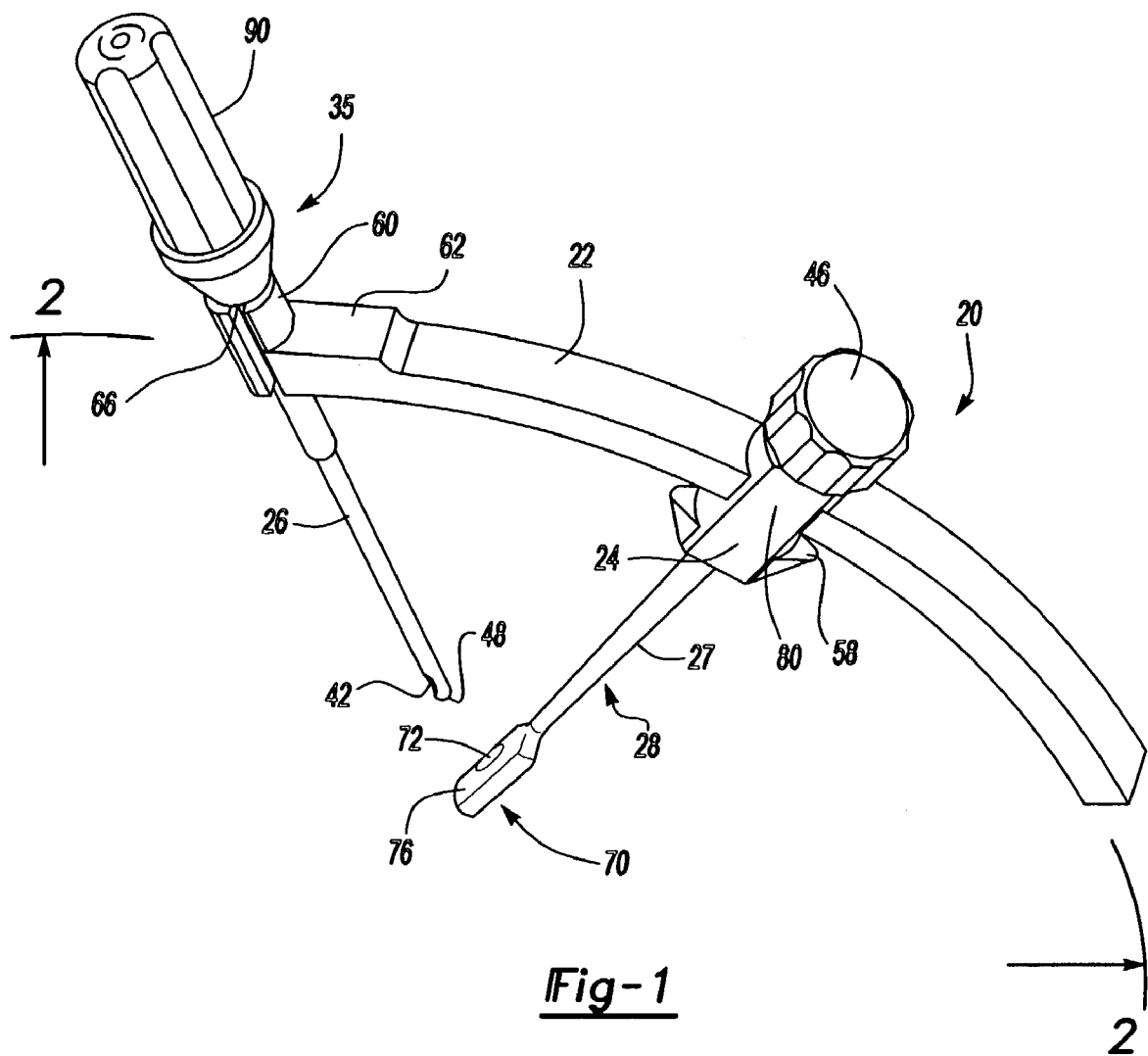
FIG. 1 illustrates a perspective view of a preferred embodiment of the present invention.
Figure 2:
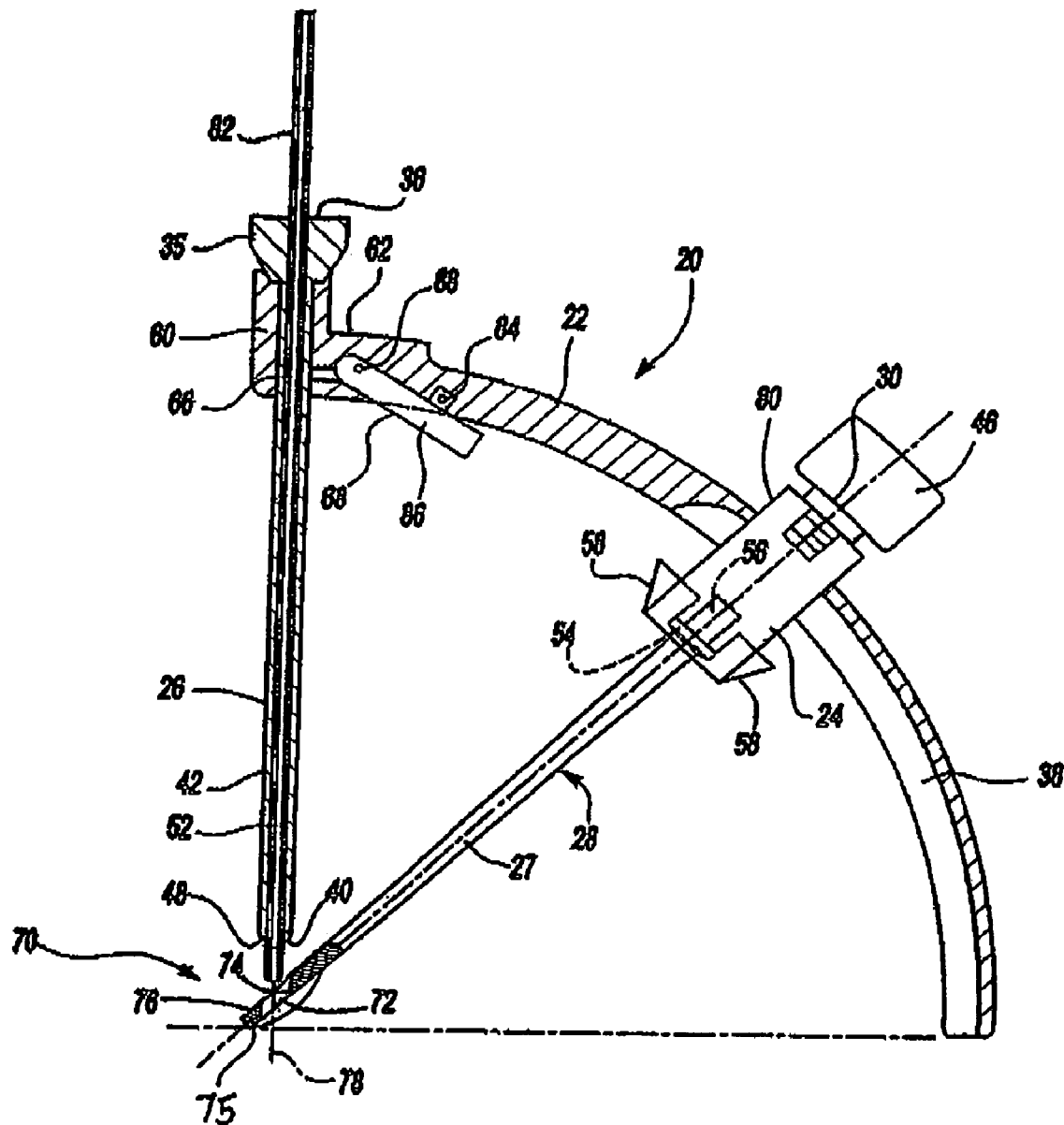
FIG. 2 illustrates a sectional view of a surgical assist device cut along line 2—2 in FIG. 1.

Sleeve guide 26, as shown in FIGS. 1, 2, and 3, includes a longitudinally extending bore 52 for receiving, for example, a guide pin 82 (such as a suture passer known in the art). At the top end of the sleeve guide 26 is a handle or knob 35 that includes an enlarged opening 36 to more easily receive surgical tools placed into bore 52. Sleeve guide 26 also has a viewing hole 42 for an arthroscopy camera to view the position of whatever is placed into bore 52. A conical shaped bottom end 48 of sleeve guide 26 has at least one tooth 40 used for gripping tissue during use and to assist in holding sleeve guide 26 in position.

Angle guide 24 as illustrated in FIGS. 1, 2, and 4 includes a base 80. Base 80 can have a hole 44 configured to receive the bow arm 22, and a slide tab 64. A threaded screw 46 is used to secure and release the angle guide 24 to and from bow 22 and lock the device at the appropriate angle. This is accomplished using frictional engagement between the base 80 and the bow arm 22 by screwing a threaded rod 30 on screw 46 into and through a threaded bore 32 until it is urged against the bow 22. Other means known in the art to secure the position of the angle guide 24 along the bow 22 are possible. Base 80 also has a target tool bore 50 having a means to secure a target tool 28, having a stem 27 and sight locator 70. Target tool 28 may also include an insertion pin 54 and a circumferential edge 56 on an end opposite sight locator 70. For this illustration, the means to secure the target tool 28 includes a pair of spring loaded locking tabs 58 known in the art connected to angle guide 24 that can releasably hold circumferential edge 56 of the target tool 28 within the target tool bore 50.

Figure 6A:
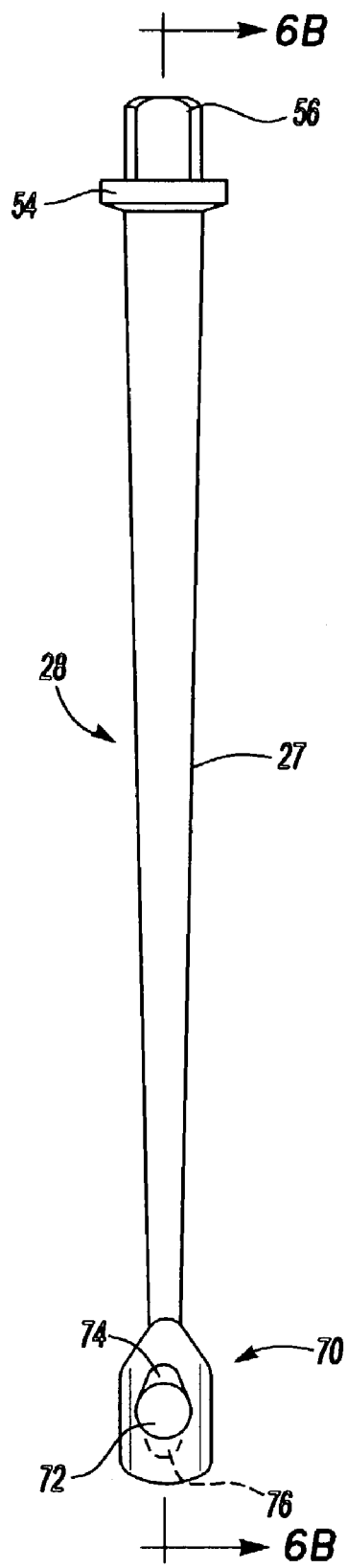
FIG. 6A illustrates a front view of a target tool of the present invention and FIG. 6B is a section cut through 6B—6B in FIG. 6A.
Figure 6B:
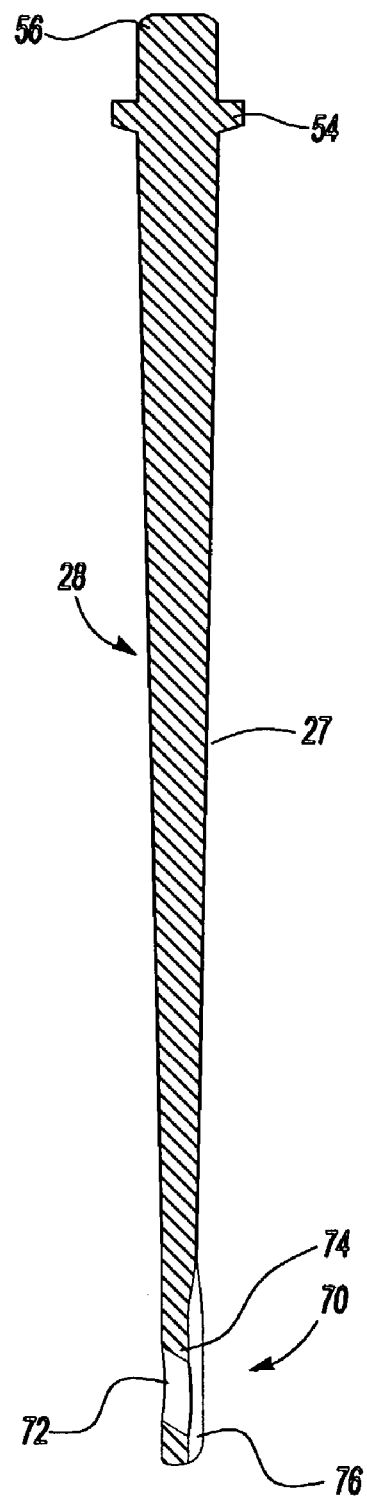

FIGS. 4, 5 and 6 show more detail of a possible target tool 28 of the present invention. As stated above, the target tool 28 is releasably attached to base 80 through the locking tabs 58 that engage and hold the circumferential edge 56 and insertion pin 54 within the target tool bore 50. As is known in the art, arthroscopic shoulder surgery requires the use of cannulas. As the present invention is adapted for use for arthroscopic shoulder surgery, target tool 28 must be adapted to fit within a cannula. As shown, target tool 28 is generally configured to be straight and narrow and adapted to be insertable through a cannula six to nine mm in diameter. Sight locator 70 is located on a second opposite end and includes an angled aperture 72. In a preferred embodiment, sight locator 70 as illustrated is generally curved having an inside floor 74 with outwardly angled curved walls 76. Curved walls 76 provide a domed shape that allow sight locator 70 to rest on the glenoid for the labrum to be repaired. Angled aperture 72 is positioned on the inside floor 74 to receive the conical shaped bottom end 48 of the sleeve guide 26. The at least one tooth 40 extends just beyond the angled walls of sight locator 70 in any position the angle guide 24 takes along the bow arm 22. One skilled in the art could develop many other types of target tool 28 having different shaped sight locator 70 and different foot angles (i.e angle of sight locator 70 in relation to stem 27). For example, as shown in FIG. 5, a target tool 28 is illustrated with sight locator 70 at an angle relative to stem 27. Sight locator 70 may also include a tooth or protrusion 75 to aid in holding sight locator 70 in the proper location as shown in the embodiment in FIG. 5. Target tool 28 may also be constructed using many different types of materials including an inexpensive sterile material that would allow it to be disposable. Target tool 28 may also be made of standard surgical steel.

As shown in FIGS. 1 and 2, bow arm 22 is arcuate shaped and can include a plurality of angle markings (not shown), and a recessed channel 38 along its length. Channel 38 slidably receives slide tab 64 of angle guide 24. Bow arm 22 fits within slide hole 44 to allow angle guide 24 to slide along bow arm 22 to a desired location.

Sleeve guide 26 is slidably and releasably attached to bow arm 22 with a sleeve guide bracket 60 on bottom portion 62 of bow arm 22. Bracket 60 includes a bracket bore 66 to which sleeve guide 26 is attached. The bracket bore 66 is configured to allow the sleeve guide 26 to slide longitudinally and perpendicular to bow arm 22. As illustrated in FIG. 2, a spring loaded release mechanism 68 can be used in conjunction with bracket 60 to secure sleeve guide 26 in the desired longitudinal location within bore 66. This mechanism 68 can have a spring 84, a lever 86, and a pivot point 88 configured to allow the spring 84 to urge the lever 86 against the sleeve guide 26 portion located within the bracket bore 66. Alternatively, a simple "set" screw type mechanism known in the art (not shown) may be used to lock sleeve guide 26 into position.

As a unit, the surgical assist device 20 has target tool 28 attached to angle guide 24, and positioned at a predetermined location along bow arm 22 such that a desired angle is achieved between target tool 28 and sleeve guide 26 based on desired suture placement location during surgery. To achieve this, the angle guide 24 and sleeve guide 26 are mounted to the bow arm 22 to point inwardly and perpendicular to the arc of the bow arm 22. The angle guide 24 and the sleeve guide 26 are also configured so that the at least one tooth 40 of the conical shaped bottom end 48 of sleeve guide 26 is at a center or intersection point 78 of the bow arm 22 arc. This is achieved by shape, configuration, and location of the angled aperture 72 and the conical shaped bottom end 48. In use, this allows the at least one tooth 40 to contact the labrum to be repaired (such as the glenoid labrum 95 shown in FIG. 7) during surgery and allow insertion of guide pins, suture placement and the like. FIG. 1 shows the surgical assist device 20 with an optional spearing tool 90 inserted through sleeve guide 26, while FIG. 2 shows optional guide pin 82 inserted through sleeve guide 26.

The device of the present invention can be used in the following method. First, an appropriate target tool 28 is chosen and is inserted into target tool bore 50 of angle guide 24 where it is held in position by the attachment described above. Angle guide 24 is then slid along bow arm 22 with slide tab 64 sliding within recessed channel 38, to the position corresponding to the selected angle. Angle guide 24 is then locked into position on bow arm 22 by tightening screw 46.

Figure 7:
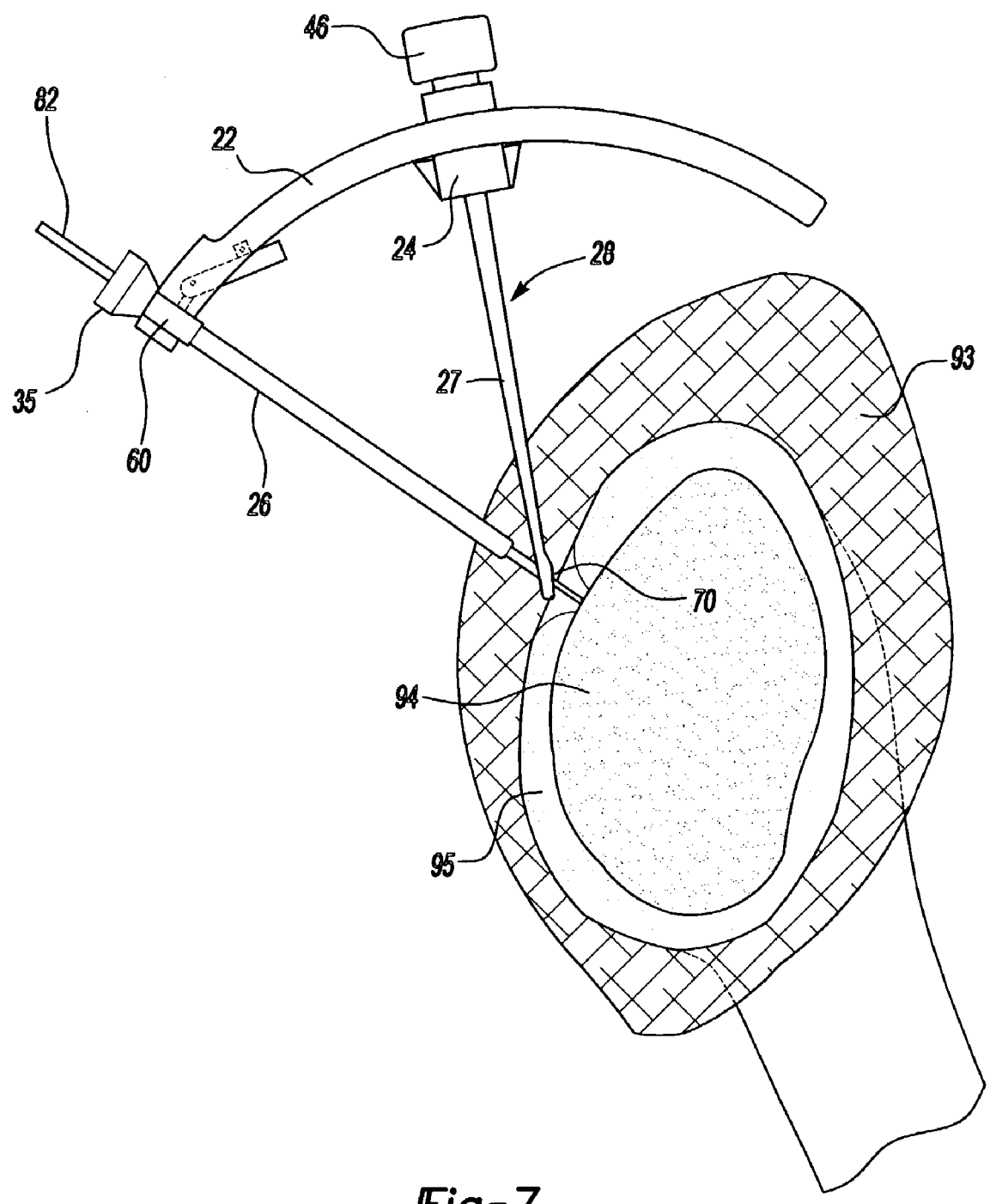
FIG. 7 illustrates the present invention positioned for use on a human shoulder.
Figure 8:
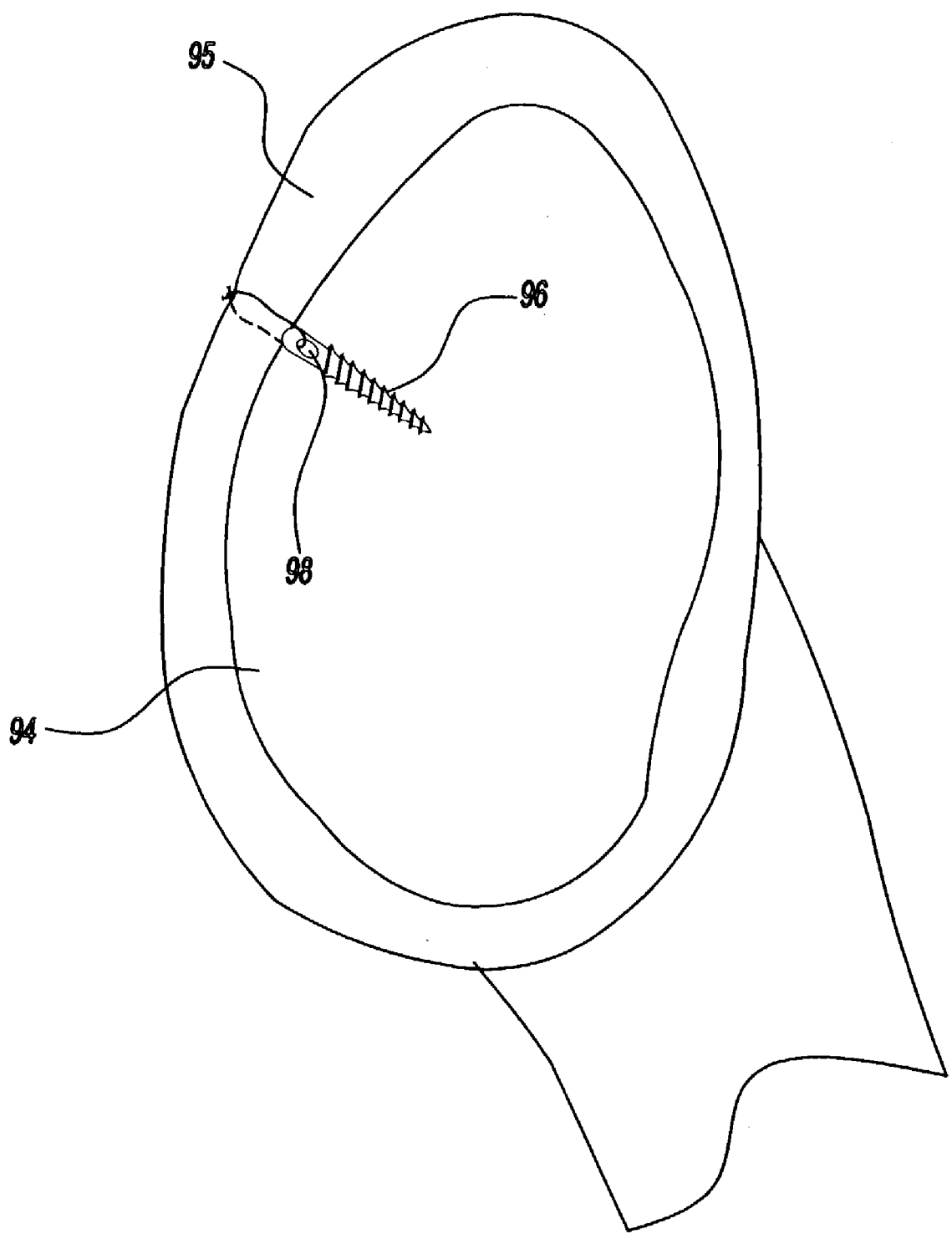
FIG. 8 illustrates an implant screw with sutures after being inserted into tissue to be repaired.

The curved sight locator 70 of target tool 28 is then inserted into the patient's glenoid cavity 93 as shown in FIG. 7 to the desired location (e.g., site of tissue reattachment). Sleeve guide 26 is then positioned longitudinally within bracket bore 66 of bracket 60 and is extended through aperture 72 of target tool 28 towards the glenoid labrum 95 until the at least one tooth 40 of conical bottom end 48 are embedded in the glenoid bone 94 and firmly holds the sleeve guide 26 in place. During positioning of sleeve guide 26, the lever 86 is depressed against the spring 84 to prevent it from pressing against the sleeve guide 26. Sleeve guide 26 is next locked into position by releasing lever 86 (or in alternate embodiments tightening a set-screw as described above).

At this point, the sleeve guide 26 has an open channel 36 to pass various tools to the tissue site needing repair. For example, guide pin 82 (such as a suture passer) can then be inserted into bore 52 of sleeve guide 26. Guide pin 82 is extended through bore 52 and through aperture 72 of target tool 28 until it contacts the glenoid bone 94. The operator can watch the progress of the guide pin 82 by pointing an arthroscopic camera (not shown) towards the viewing hole 42. Sleeve guide 26 can then be removed, leaving guide pin 82, in position.

In one procedure, a guide pin 82 may include a tap drill to drill a hole to receive a screw followed by placement of a screw having sutures attached thereto. The screw 96, may be made of biodegradable material or titanium and can penetrate and attach to the glenoid bone 94. The screw 96 typically has an eyelet 98 through which a strong suture is pre-threaded. Once the screw is in place and the sleeve guide 26 and guide pin 82 are removed, the sutures remain hanging through aperture 72. As the target tool 28 is next removed, the sutures can be pulled through the glenoid labrum 95 and exit the patient at the site of entry of the target tool. This process aids the surgeon in tying the sutures to secure damaged tissue back to the bone. As shown in FIG. 7, once the surgeon has tied-off the suture ends, the suture securely holds the labrum 95 to the glenoid bone 94. This process can be repeated for each site of attachment needed for the patient.

Some clear advantages of the surgical assist device 20 of the present invention is the use of the at least one tooth 40 to hold the sleeve guide 26 in place, thus firmly holding the sleeve guide 26 in the correct position. The bow arm 22 ensures that guide pin 82 and aperture 72 will always intersect to allow the at least one tooth 40 to be placed in the proper position, irrespective of where angle guide 24 is positioned along bow 22. When used with an arthroscopic camera, the target tool 28 allows the surgeon to quickly and efficiently locate where to place the sleeve guide 26 by removing guesswork, trial and error, and tissue damage formerly associated with this type of shoulder surgery. The angled aperture 72 allows sutures to be brought to position to allow the surgeon to tie them off. The curved edge of the curved sight locator 70 allows for easier placement of the sleeve guide 26 during use.

Various alterations and changes can be made to the illustrated embodiment of the present invention without departing from the spirit and broader aspects of the invention as set forth in the appended claims, which are to be interpreted in accordance with the principles of patent law, including the doctrine of equivalence.

We claim:

1. An arthroscopic shoulder surgical assist device, comprising:

an arcuate shaped bow arm;

an angle guide releasably attached to the bow arm at selected locations along the arc of the bow arm;

a sleeve guide having a base end slidably attached to the bow arm and a tip end having at least one tissue gripping tooth, the sleeve guide further having a longitudinally extending bore;

a target tool releasably, fitting within a cannula; connected to the angle guide at a first end and including a second end extending away from the bow arc having an aperture, wherein the tip end of the sleeve guide extending to intersect and pass through the aperture positioned on the inside of a domed shape sight locator, of the target tool irrespective of the position of the angle guide on the bow arm; and wherein the at least one of said tooth on the tip end of the sleeve guide is adapted to be embedded in a glenoid bone of a shoulder.

2. The surgical assist device as defined in claim 1, wherein the at least one tooth includes a plurality of teeth.

3. The surgical assist device as defined in claim 1, wherein the releasable attachment of the angle guide includes a threaded screw extending through the angle guide and engaging the bow arm.

4. The surgical assist device as defined in claim 1, wherein the second end includes curved walls and a floor, wherein the aperture is located on the floor.

5. The surgical assist device as defined in claim 1, wherein the first end includes a pin.

6. The surgical assist device as defined in claim 5, wherein the pin is inserted into a hole in the angle guide to attach the target tool to the angle guide.

7. The surgical assist device as defined in claim 1, wherein the target tool is made of a disposable material.

8. The surgical assist device as defined in claim 1, wherein the target tool is made of surgical steel.

9. The surgical assist device as defined in claim 1, wherein the target tool includes a stem portion connecting the first and second end and the second end is angled in relation to the stem.

10. The surgical assist device as defined in claim 1, wherein the angle guide includes a viewing hole.

11. The surgical assist device as defined in claim 1, wherein the second end further includes a protrusion extending outward toward the glenoid bone.

12. A method for locating a target location for a glenoid labrum lesion repair in arthroscopic shoulder surgery using a surgical assist device, the surgical assist device comprising an arcuate shaped bow arm, an angle guide releasably attached to the bow arm at selected locations, a sleeve guide attached to the bow arm, a target tool, configured to fit within a cannula used for arthroscopic shoulder surgery, attached to the angle guide at a first end of the target tool and including a second end having an aperture, and the sleeve guide extending outward from the bow arm and having at least one tooth on the second end and a longitudinally extending bore, the method comprising the steps of:
  inserting the second end of the target tool into a glenoid cavity of a shoulder requiring lesion repair;
  positioning the aperture of the target tool at a desired location; and
  advancing the sleeve guide towards the glenoid labrum and through the aperture of the target tool until the at least one tooth on the sleeve guide contacts a glenoid bone and is embedded in the glenoid bone, firmly holding the sleeve guide in position.

13. The method of claim 12 further including the step of positioning the angle guide at a select location such that a desired angle is achieved between the target tool and the sleeve guide.

14. The method of claim 12 further including the step of inserting a guide pin through the longitudinally extending bore of the sleeve guide and into the glenoid bone.

15. The method of claim 14, wherein the guide pin includes a screw and sutures and wherein the screw is inserted through the glenoid bone, and the sutures are connected to the screw and have ends that hang therefrom and through the aperture of the target tool.

16. The method of claim 15 further including the step of removing the target tool from the glenoid cavity, thereby pulling the ends of the sutures out through the glenoid labrum, exposing and providing access to the ends of the sutures.

17. The method of claim 15, wherein the screw is made of biodegradable material.

18. The method of claim 15, wherein the screw is made of titanium.

* * * * *